United States Patent [19]

Irie et al.

[11] Patent Number: 4,557,931

[45] Date of Patent: Dec. 10, 1985

[54] ANTIGENIC COMPOSITIONS AND METHODS FOR USING SAME

[75] Inventors: Reiko F. Irie; Tadashi Tai; Donald L. Morton; Leslie D. Cahan; James C. Paulson, all of Los Angeles, Calif.

[73] Assignee: Regents of the University of California, Berkeley, Calif.

[21] Appl. No.: 446,231

[22] Filed: Dec. 2, 1982

[51] Int. Cl.[4] ...................... A61K 39/00; G01N 33/54
[52] U.S. Cl. ........................................... 424/88; 435/7
[58] Field of Search ......................................... 424/88

[56] References Cited
PUBLICATIONS

Tai et al.–Chem. Abst. vol. 99 (1983) pp. 137, 909s.
Jonah et al.–Chem. Abst. vol. 89 (1978) pp, 104, 517c.
Young et al.–Chem. Abst. vol. 92 (1980) p. 39574g.
Uchida et al.–Chem. Abst. vol. 94 (1981) p. 26466x.
Chem. Abst. Subj Index–10th Collect (1977–1981) pp. 23060cs and 26062cs.

*Primary Examiner*—Sam Rosen
*Attorney, Agent, or Firm*—Poms, Smith, Lande & Rose

[57] ABSTRACT

GM2 is a ganglioside present on the surface of tumors and stimulates an appreciable immune response in mammals. It is useful when coupled with a non-toxic protein carrier or mixed with an adjuvent and injected parenterally of raising the anti-GM2 titer in serum. GM2 is also valuable as a diagnostic agent.

12 Claims, No Drawings

ANTIGENIC COMPOSITIONS AND METHODS FOR USING SAME

This invention was made with Government Support under Grant Nos. CA 12582 and CA 30647 awarded by the Department of Health and Human Services. The Government has certain rights in this invention.

BACKGROUND OF THE INVENTION

Gangliosides are complex sphingolipids which are found in highest concentration in the nervous system. They are composed of an oligosaccharide chain containing an acidic sugar attached to ceramide. GM2 is a rare ganglioside which is present, in very low amounts, in normal brain tissue, whose structure is as follows:

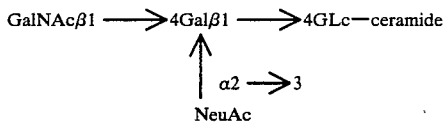

wherein GalNAc is N-acetylgalactosamine, Gal is galactose, Glc is glucose and NeuAc is N-acetylneuraminate.

We have found that this ganglioside, GM2, is present on or in human tumors of a variety of histological types including melanoma, brain tumors, lung carcinomas, sarcoma and breast carcinomas. The GM2 ganglioside is present on the surface of tumors and stimulates an appreciable immune response in mammals.

As reported in the publications identified as references 1 through 15 set forth in Table I, a composition, eventually called OFA-I was found to induce humoral immune responses in cancer patients.

GM2 was identified by use as being an active antigen present in OFA-I. In vitro tests have demonstrated that anti-OFA-I antibody is cytotoxic to tumor cells in the presence of human complement (References 8 and 9, Table I).

Reference 14 in Table I discloses the production of mono-specific human anti-OFA-I in vitro by the use of human B-lymphocytes transformed by Epstein-Barr virus.

Reference 4 in Table I discloses the OFA-I on tumor cells is immunogenic but the chemical nature of the antigenic determinant of OFA-I is not known.

Reference 15 in Table I discloses an attempt to determine and purify the antigenic determinant in OFA-I by concentrating the culture medium, filtering the concentrate and then extracting with a mixture of chloroform and methyl alcohol. There was obtained a soluble portion, an insoluble portion and a precipitate. It was found that the insoluble portion contained oncofetal antigens (OFA) and the soluble portion contained tumor associated antigens (TAA). The soluble and insoluble portions were then subjected into a 5–30% sucrose density radiant ultra-centrifugation. Peak activity of OFA was found to be present in the 17% sucrose region and peak activity of TAA was in the 12.5% sucrose.

The article on page 354 states that even though OFA and TAA can be separated by chloroform-methyl alcohol extraction, the fraction containing the OFA was "not absolutely pure". On page 355 the authors state that the "exact chemical nature of the OFA . . . defined and isolated . . . is unknown at this time."

All of the publications of which we are aware thought that OFA-I, as defined by serum antibodies, contained only one antigenic specific determinant which was present on tumor cells and was immunogenic. However, it was recently discovered by us of the monospecific antibodies produced in vitro by human B-limphoblastoid cell lines that there are, in fact, at least two specific antigenic determinants in OFA-I, GM2 and another ganglioside which is also immunogenic and present on human tumor cells.

In addition to these two antigens, OFA-I, even when semi-purified as set forth in reference 15, contains a number of antigenic compounds (e.g. glycolipids and phospholipids) which makes OFA-I unsuitable for use as a diagnostic or therapeutic agent because of interference of the other antigenic compounds.

In addition, insofar as we are aware, antibodies produced by other gangliosides, when injected into mammals, adversely affect the nervous system. This is not the case with anti-GM2, presumably because GM2 is only present in small amounts on the surface of the brain cells.

SUMMARY OF THE INVENTION

We have discovered that the ganglioside GM2 is the active antigenic determinant in OFA-I which is immunogenic and which is present on tumor cells of the histologic type mentioned above.

GM2 cannot be obtained from natural sources since it is present in extremely small amounts in normal tissues and, insofar as we are aware, other gangliosides would not be removed. Accordingly, we have invented a method for producing GM2, which is relatively simple and inexpensive and renders available large quantities of GM2 for therapeutic and diagnostic uses. The starting material for producing GM2 is an abundant ganglioside GM1 which has the structural formula:

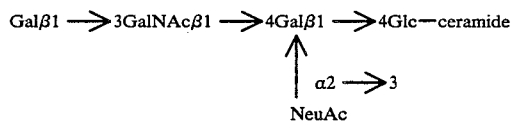

Although OFA-I has been used experimentally in stage II melanoma patients and it did raise the anti-OFA-I titer, the possibility of side effects and interference with other antigenic determinants in OFA-I, makes it impossible to use OFA-I for such purposes, other than experimental. Accordingly, if GM2 having no other antigens is conjugated with a non-toxic protein carrier, such as albumin (preferably serum albumin) or by admixing GM2 with one or more adjuvants which stimulate immune response (hereinafter stimulative immune response adjuvants) such as liposomes (hereinafter such mixtures will sometimes be referred to as antigenic compositions) it would be an excellent vaccine which will raise the anti-GM2 titer in mammals, e.g. humans. In this regard it is noted that it is the oligosaccharide portion of GM2 which is antigenic and that prior to coupling GM2 to the non-toxic protein carrier either the entire ceramide portion of GM2 may be removed (in which event the oligosaccharide of GM2 is coupled through the glucose moiety) or the fatty acid of the ceramide may be removed leaving sphingosine (in which event the oligosaccharide of GM2 is coupled through the amine group of the sphingosine moiety).

It is known that patients which have high anti-OFA-I titer have high survival rates after surgery. Accordingly, the antigenic GM2 conjugate or the GM2-liposome antigenic composition may be used as a vaccine to immunize cancer patients having histological type tumors bearing GM2 or as a preventive vaccine to treat non-cancerous persons in order to prime the immune system to react against GM2 bearing tumor cells which may appear. Such vaccine may be administered parenterally, e.g. intradermally or intralymphatically.

The pure GM2, the conjugated GM2 or the GM2 antigenic composition are all useful as diagnostic agents. For example, heretofore skin tests have been used to monitor the effectiveness of immunotherapy in cancer patients. This type of reaction is the most desirable for combatting tumor cells. However, heretofore it has not been possible to test for cell-mediated immunity directed against a specific antigen. The purified GM2, the conjugated GM2 or the GM2 antigenic composition all may be used for conducting such type of skin tests, and are particularly useful to test the effectiveness of the immunization using the GM2 vaccine as described above.

Another diagnostic use for the pure GM2 (i.e. GM2 having no other antigenic determinants) is to test for circulating (humoral) antibodies. As has been stated heretofore, it is known that patients having the histological type tumors will have circulating anti-GM2. Thus, the pure GM2 may be utilized in an immunoassay method for determining the amoiunt of anti-GM2 in the serum of patients. The immunoassay method will include determining the amount of anti-GM2 present in a liquid sample (e.g. serum) by mixing with the liquid sample containing the unknown amount of anti-GM2 an amount of pure GM2, said amount being either more than the amount of anti-GM2 or less than the amount of anti-GM2 and allowing said liquid sample containing anti-GM2 and pure GM2 to incubate until reaction between said anti-GM2 and pure GM2 and then measuring the amount of one of the following: (1) the amount of unreacted pure GM2, (2) the amount of unreacted anti-GM2, or (3) the amount of the reaction product between anti-GM2 and GM2.

Although the quantitative amount of said products may be measured in any of the numerous methods known to the art, it is preferred if such measurement is done by utilizing a marker which is easy to measure quantitatively because of its activity (e.g. the marker may be an enzyme; a fluorescent molecule which emits light upon excitation by an appropriate light source; a chemiluminescent molecule which will emit light after a chemical reaction such as oxidation; a radioactive molecule; etc.) is linked or bound to either the antibody or the antigen or the antibody-antigen conjugate.

One of the simplest methods is to add serum, containing anti-GM2, to a plastic well which is coated with a small amount of pure GM2. The antibodies bind to the GM2 in the plastic well and the serum is then washed out of the well. The antibodies bound to the antigen are then quantitatively measured by reacting the bound antibody with a marker such as Protein A or anti-human immunoglobulins labelled with a radioisotope or conjugated to enzymes (alkaline phosphatase).

Another diagnostic method of the present invention to determine cancer is to utilize anti-GM2. We have determined that GM2 is shed from GM2 bearing tumor cells in tissue culture and GM2 bearing tumor cells in patients shed GM2 in the serum. Therefore, using the same method as described above, the amount of GM2 in the serum may be measured by utilizing anti-GM2.

Another diagnostic test, which this invention is ideally suited, is tissue typing. By this we mean testing a tumor biopsy for the presence of GM2. This type of test is important for a number of reasons, one of the most important being to determine the effectiveness of immune therapy since tumors devoid of GM2 will be unaffected by an immune response directed against it. Moreover, utilizing such tissue typing will enable one to determine whether such tumor is cancerous by determining whether such tumor has GM2 antigens thereon. Thus, the tissue will be contacted with anti-GM2 and then it will be determined whether the anti-GM2 has reacted with the tumor cells by measuring the amount of anti-GM2 bound by direct or indirect methods.

One specific indirect method for accomplishing tissue typing is to mix anti-GM2 with the tissue homogenate to be tested for GM2 and the mixture applied to a plastic well coated with GM2. If no GM2 is present in the tissue samples the antibodies will bind to the well and after the remaining samples are washed away they can be detected as discussed above. If GM2 is present in the tissue sample the antibodies will be bound to the tissue antigen and therefore be unable to bind to the pure GM2 coating of the plastic well. Thus, when the sample is washed away, no antibodies will be detected. Some specific direct methods of determining the amount of GM2 present in tumors would be to determine the binding of anti-GM2 labeled with a marker to frozen tissue sections or to tumor cells in a tissue homogenate. For frozen tissue, anti-GM2 would be overlayed on tissue sections and after incubation, unreacted anti-GM2 would be washed away. The amount, if any, of bound anti-body would then be determined by measuring the amount of marker, e.g. by a fluorescent or a light microscope.

For tissue homogenate, anti-GM2 would be added and the mixture incubated. The tumor cells would be collected by centrifugation and anti-body bound to the cells would be quantitated by measuring the amount of the marker present on the cells or the amount of marker depleted from the supernatant.

DESCRIPTION OF THE PREFERRED EMBODIMENTS

A. Method of making GM2

The general method for the production of the antigenic ganglioside GM2, which is free of other antigenic determinants (hereinafter pure GM2) has been set forth above. Such method's starting point is GM1 which is relatively easy and inexpensive to obtain. The GM1 is first dissolved in an aqueous solution.

The terminal galactose residue of GM1 is removed, to form GM2, by using an enzyme effective amount of beta-galactosidase (preferably lysomal beta-galactosidase). The thus formed GM2 may be separated from the solution by any of a number of methods including chromatography on silica gel.

We have found that the reaction is much more efficient if it is conducted in the presence of a surfactant. We have also found that a very effective surfactant is a metal (preferably an alkali metal) salt of taurocholic acid. The surfactant is preferably present in an amount of between about 3 to 10 parts by weight, based on one part by weight of the starting ganglioside.

In the preferred method the beta-galactosidase used is bovine testes beta-galactosidase prepared as described in Reference 16, Table I.

A reaction solution (1.0 ml) is prepared containing 1 mg. of GM1 and 1 mg. of delipidized bovine serum albumin in 0.01 solar potassium acetate (pH 5.0), 1 wt. % sodium taurocholate and 0.4 units of bovine testes beta-galactosidase. The solution is incubated at 37° C. The reaction is greater than 95% in 29 hours. The reaction mixture, after 29 hours, is lyophilized and the gangliosides, GM1 and GM2, are desalted on a column containing 1.0 gram Sephadex G-25 and eluted.

The eluate is purified by preparative thin layer chromatography in chlorofrom:methanol:water (1.0:2.0:1.4, vol.). Pure GM2 is eluted from the silica by extraction into chloroform:methanol (1:2, vol.) overnight at room temperature (25° C.).

B. GM2 Vaccine

As noted hereinbefore the GM2 vaccine may be of two types: (1) GM2 conjugated to a non-toxic protein carrier and (2) an antigenic composition consisting essentially of pure GM2 and a stimulative immune response adjuvent such as liposome or methylated human serum albumin.

The pure GM2 is conjugated to an appropriate non-toxic carrier such as human serum albumin using the oligosaccharide of GM2 which is released by ozonolysis. One mg. of GM2 is dissolved in 1.5 ml. of absolute methanol. Ozone is bubbled through the solution at room temperature. The methanol is then evaporated off and after the methanol is removed, one ml. of 0.1 molar sodium hydroxide is added. After 16 hours at room temperature, the sample is neutralized by passage through a column of Dowex 50W-X8 resin (H$^-$ form). The eluate is lyophilyzed, the residue is dissolved in 0.002 molar pyridine acetate buffer, pH 5.4, and applied to a column of DEAE-cellulose equilibrated with the same buffer. The oligosaccharide is eluted with 1.0 molar pyridine acetate, pH 5.4, and the eluate lyophilyzed. This yields about 0.5 mg. of the oligosaccharide portion of GM2.

The oligosaccharide is reacted with beta(p-aminophenethyl)ethyl amine by mixing the two together at room temperature to form a Schiff's base conjugate. Sodium borohydride in ethanol is then added to the conjugate to reduce the conjugate, yielding an irreversible bond.

After destruction of excess sodium borohydride by lowering the pH to 5.0 with glacial acetic acid, the ethanol is removed under vacuum and the resulting conjugate is separated from the free amine by chromatography on a column of Sephadex G-10.

The now-purified conjugate is linked with thiophosgene and after removal of the excess thiophosgene by extraction with chloroform, the isothiocyanate derivative is added to an equal volume of 0.3 molar sodium chloride in 0.1 molar sodium carbonate (pH 9.5) containing human serum albumin. The mixture is incubated about 18 hours at room temperature and the GM2 oligosaccharide-albumin conjugate is purified by chromatography on a column of Sephadex G-75.

In order to use the conjugate as a vaccine for humans it should be dissolved in an aqueous solution which is non-toxic (e.g. about one to 10 mg. per ml. of saline). The solution is parenterally injected (about 5 cc.) every two weeks until high antibody titer appears in the blood.

In order to use the conjugate as a diagnostic agent for skin tests, e.g. to determine the effectiveness of the vaccine in cell mediated delayed hypersensitive, the vaccine solution is injected intradermally (about 0.5 ml. per site). After about two days the patient is examined to see if red spots appear at the injected sites, which indicate the presence of cell mediated immune response.

The GM2 antigenic composition may be made by mixing pure GM2 with liposome consisting of dimyristoylphosphatidylcholine (DMPC), cholesterol and dicetyl phosphate in molar ratios of 2:1.5:0.22 in a ratio of 0.15 mg. GM2 to one mg. of DMPC. The resulting mixture is a vaccine which is used in the same way as the protein conjugate.

The liposome-GM2 antigenic composition may, in general, consist of one part by weight of GM2 and from about one to 20 parts by weight of liposome or any other adjuvent known to stimulate immune response.

Another adjuvant very useful in the present invention is non-toxic lipid A which may be used per se with GM2 or, preferably, with the liposome-GM2 antigenic composition. For example, 5 weight parts of lipid A may be mixed with the liposome composition to produce an excellent vaccine for therapy of cancer patients or in prevention of cancer.

C. Diagnostic Tests

Pure GM2 is adsorbed on the walls of polystyrene microtiter plates by contacting with an aqueous phosphate buffered saline solution of GM2 (about 1.5 mg. per ml.). The thus coated microtiter plates are then contacted with 0.05 ml. of serum from a human patient and allowed to incubate at room temperature for about twelve hours. The serum is washed off the plates with phosphate buffered saline solution and the washed microplates are then overlayed with a solution containing a marker for anti-GM2. The plates are then incubated for an hour at 25° C. The overlay is removed by washing any marker remaining on the plate measured by an approximate instrument which will show the presence or absence of anti-GM2 in the serum.

TABLE I

References

1. Irie, R. F. and Morton, D. L.: A new membrane antigen on human cultured cells. Proc. Amer. Assoc. Cancer Res. 16:171, 1975.
2. Irie, R. F. Irie, K. and Morton, D. L.: A membrane antigen common to human cancer and fetal brain tissues. Cancer Res. 36:3510–3517, 1976.
3. Irie, K., Irie, R. F. and Morton, D. L.: Humoral immune response of patients with malignant melanomas: Melanoma associated membrane antigens demonstrable by indirect membrane immunofluorscence. Cancer Immunol. Immunother. 6:33–39, 1979.
4. Irie, R. F.: Oncofetal antigen (OFA-I): A human tumor-associated fetal antigen immunogenic in man. In: *Serologic Analysis of Human Cancer Antigens* (S. Rosenberg, ed.) Academic Press, New York, 1980, pp. 493–513.
5. Rees, W. V., Irie, R. F. and Morton, D. L.: Oncofetal antigen (OFA-I): Distribution in human tumors. J. Natl. Cancer Inst. 67:557–562, 1981.
6. Irie, R. F., Giuliano, A. E. and Morton, D. L.: Oncofetal antigen (OFA): A tumor associated fetal antigen immunogenic in man. J. Natl. Cancer Inst. 63:367–373, 1979.

7. Sidell, N., Irie, R. F. and Morton, D. L.: Immune cytolysis of human malignant melanoma by antibody to oncofetal antigen-I (OFA-I). II. Antibody-dependent cell-mediated cytotoxicity. Cancer Immunol. Immunother. 9:49–54, 1980.

8. Sidell, N., Irie, R. F. and Morton, D. L.: Oncofetal antigen: A target for immune cytolysis of human cancer. Brit. J. Cancer 40:950–953, 1979.

9. Sidell, N., Irie, R. F. and Morton, D. L.: Immune cytolysis of human malignant melanoma by antibody to oncofetal antigen-I (OFA-I). I. Complement dependent cytotoxicity. Cancer Immunol. Immunother. 8:211–214, 1980.

10. Jones, P. C., Sidell, N., and Irie, R. F.: Embryonic antigens in tumor cytolysis (editorial). Cancer Immunol. Immunother. 8:211–214, 1980.

11. Jones, P. C., Sze, L. L., Morton, D. L. and Irie, R. F.: Prolonged survival for melanoma patients with elevated IfM antibody to oncofetal antigen (OFA-I). J. Natl. Cancer Inst. 66:249–254, 1980.

12. Irie, R. F., Jones, P. C. and Morton, D. L.: Prolonged survival of melanoma patients with high titers of antibody to oncofetal antigen (OFA-I). Proc. Fourth Int. Conf. Immunol. 10.5.35, 1980.

13. Ahn, S. S., Irie, R. F., Weisenburger, T. H., Jones, P. C., Juillard, G. J. F., Denise, J. R. and Morton, D. L.: Humoral immune response to intralymphatic immunotherapy for metastatic melanoma: Correlation with clinical response. (In press).

14. Irie, R. F., Jones, P. C., and Morton, D. L.: In vitro production of human antibody to a tumor-associated fetal antigen. Brit. J. Cancer 44:262–266, 1981.

15. Gupta, R. K., Irie, R. F., Chee, D. O., Kern, D. H., and Morton, D. L.: Demonstration of two distinct antigens in spent tissue culture medium of human malignant melonoma cell line. J. Nat, Cancer Inst. 63:359–366, 1980.

16. Distler, J. J. and Jourdian, G. W.: The purification and properties of β-galactosidase from bovine testes. J. Biol. Chem. 248: 6772–6780, 1973.

We claim:

1. An antigenic conjugate which is immunoreactive with anti-GM2 antibodies produced by mamallian tumors said antigenic conjugate consisting essentially of the oligosaccharide portion of GM2 conjugated to a non-toxic mammal compatible protein carrier.

2. An antigenic conjugate according to claim 1 wherein the conjugated bond between said oligosaccharide and said non-toxic protein carrier is formed by the glucose moiety of the oligosaccharide.

3. An antigenic conjugate according to claim 1 wherein the conjugated bond between said oligosaccharide and said non-toxic protein carrier is formed by the amine group of the sphingosine moiety of the ceramide portion of GM2.

4. An antigenic conjugate according to claim 1 wherein the protein carrier is human serum albumin.

5. A vaccine, which when parenterally injected into a mammal, will raise the anti-GM2 titer in the blood of said human, said vaccine consisting essentially of an antigenic conjugate selected from the antigenic conjugate according to claim 1, claim 2, claim 3 or claim 4, said antigenic conjugate being dissolved in a non-toxic aqueous solution.

6. A vaccine according to claim 5 wherein the non-toxic aqueous solution is saline solution.

7. A vaccine according to claim 6 wherein the antigenic conjugate is present in an amount of between about one to 10 mg. per ml. of saline solution.

8. A method for increasing the anti-GM2 titer in mammals which comprises parenterally injecting into said mammals an anti-GM2 increasing titer effective amount of a composition according to claims 6 or 7.

9. A method for increasing the anti-GM2 titer in mammals in need of anti-GM2 therapy which comprises parenterally injecting into said mammals an anti-GM2 increasing titer effective amount of an antigenic composition which is immuno-reactive with anti-GM2 antibodies produced by mammalian tumors, said antigenic composition consisting essentially of pure GM2 and a non-toxic stimulative immune response adjuvant.

10. A method according to claim 9 wherein the stimulative immune response adjuvant is liposome.

11. A method according to claim 9 wherein the stimulative immune response adjuvant is lipid A.

12. A method according to claim 9 wherein the non-toxic stimulative immune response adjuvant is present in an amount of between about one to 20 parts by weight based on one part by weight of pure GM2.

* * * * *